US006338966B1

(12) United States Patent
Falco et al.

(10) Patent No.: US 6,338,966 B1
(45) Date of Patent: *Jan. 15, 2002

(54) GENES ENCODING SULFATE ASSIMILATION PROTEINS

(75) Inventors: Saverio Carl Falco, Arden; Stephen M. Allen, Wilmington, both of DE (US); Shawn L. Anderson, West Grove, PA (US); J. Antoni Rafalski, Wilmington, DE (US)

(73) Assignee: E. I. du Pont de Nemours & Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/346,408

(22) Filed: Jul. 1, 1999

Related U.S. Application Data

(60) Provisional application No. 60/092,833, filed on Jul. 14, 1998.

(51) Int. Cl.$^7$ .......................... C07H 21/04; C12N 9/12; C12N 1/20; C12N 15/00; C12N 15/74

(52) U.S. Cl. .................. 435/471; 435/476; 435/252.3; 435/320.1; 435/6; 435/194; 536/23.2

(58) Field of Search ............................ 435/194, 320.1, 435/6, 252.3, 474, 471, 476; 536/23.2

(56) References Cited

PUBLICATIONS

Klonus et al., Plant J., 6(1), 105–112, Jun. 1994.*
Carmen Rotte et al., Plant Physiology, vol. 124:715–724, 10/2000, Differential Subcellular Localization and Expression of ATP Sulfurylase and 5′–Adenylylsulfate Reductase During Ontogenesis of Arabidopsis Leaves Indicates That Cytosolic and Plastid Forms of ATP Sulfurylase May Have Specialized Functions.
Smith et al., (1995) PNAS U.S.A. 92(20):9373–9377.
Bolchi et al. (1999) Plant Mol. Biol. 39(3):527–537.
Arz et al. (1994) Biochim. Biophy. Acta 1218(3):447–452.
Setya et al. (1996) PNAS U.S.A. 93(23):13383–13388.
Saito et al. (1995) J. Biol. Chem. 270(27):16321–16326.
NCBI General Identifier No. g2738750, Mar. 31, 1999.
NCBI General Identifier No. g479090, Aug. 22, 1994.
Plant J. 6(1), pp. 105–112 (1994).
NCBI General Identifier No. g629733, Apr. 12, 1996.
NCBI General Identifier No. g629562, Mar. 15, 1996.
Keiko Yonekura–Sakakibara et al., (1998) J. Biochem. 124, 615–621.
Sasaki T., EMBL Database, Aug. 6, 1997, *Rice CDNA from callus*, XP00212812.
MBEGUIE–A–MBEGUIE D. et al., EMBL Database, Jun. 29, 1998, XP002128211.
Ideguchi T. et al., EMBL Database, Jan. 1, 1998, XP002128212.
Bork C. et al., "Isolation and characterization of a gene for assimilatory sulfite reductase from *Arabidopsis thaliana*" Gene: An International Journal On Genes And Genomes, vol. 212, No. 1, May 28, 1998, XP004122435.
Bruhl A. et al., "A CDNA clone from *Arabidopsis thaliana* encoding plastidic ferredixon: sulfite reductase" Biochimica et Biophysica Acta, vol. 1295, 1996, pp. 119–124, XP002121813.
Database WPI, Section Ch, Week 199440, Derwent Publications Ltd., London, GB; p. 6, An 1994–321282, XP002121814.
Smith F. et al., Plant J., vol. 12, No. 4, 1997, pp. 875–884, XP002129909.
Sohlberg L. and Sussex I., EMBL Database, Jul. 1997, XP002129910.
Federspiel N. et al., EMBL Database, Jun. 1998 XP00212911.
Minobe Y. and Sasaki, T., EMBL Database, XP002129912, Nov. 1993.
Bolchi A. et al., EMBL Database, Jan. 8, 1998 XP002121790.
Ng et al., sulfate transporter from *Sporobulus stapfianus*, EMBL Database, Mar. 1997, XP002121791.
Takahashi et al., Regulation of sulfur assimilation in higher plants PNAS U.S.A. (Sep. 30, 1997) XP002121792.
Smith et al. "Plant members of a family of sulfate transporters reveal functional subtypes" PNAS, avol. 92 (1995) p. 9373–9377 XP002129913.
Arz, H. E. et al., Biochimica et Biophysica ACTA, vol. 1218, No. 3, Aug. 1994, pp. 447–452, XP000853523.
Bick, J.A. and Leustek, T., Current Opinion in Plant Biology, vol. 1, No. 3, Jun. 1998, pp. 240–244, XP000853523.
Schiffmann, S. & Schwenn, J.D., FEBS Letters, vol 355, 1994, pp. 229–232, XP002122477.
Jain, A. & Leustek, T., Plant Physiology, vol. 105, 1994, pp. 771–772, XP002122478.
Chen, Y. & Leustek, T., Plant Physiology—Supplement, vol. 108, No. 2, Jun. 1995 p. 72, XP002122479.
Lee, S. and Leustek, T., Biochemical and Biophysical Research Communications, vol. 247, Jun. 9, 1998 pp. 171–175, XP00212248.
Walbot, V.m EMBL Sequence Data Library, Apr. 27, 1999, XP002123195.
Saito K. et al., The Journal od Biological Chemistry, vol. 270, No. 27, 1995, pp. 16321–16326, XP002115631.

(List continued on next page.)

Primary Examiner—Rebecca E. Prouty
Assistant Examiner—Maryann Monshipouri

(57) ABSTRACT

This invention relates to an isolated nucleic acid fragment encoding a sulfate assimilation protein. The invention also relates to the construction of a chimeric gene encoding all or a portion of the sulfate assimilation protein, in sense or antisense orientation, wherein expression of the chimeric gene results in production of altered levels of the sulfate assimilation protein in a transformed host cell.

12 Claims, 3 Drawing Sheets

OTHER PUBLICATIONS

Roberts M. et al., Plant Molecular Biology, vol. 30, 1996, pp. 1041–1049, XP002115633.

Sasaki T., EMBL Database, Aug. 6, 1997, XP002128627.

Saito K. and Takagi Y, EMBL Database, May 1, 1997, XP002128628.

Yoo B. and Harmon A., Plant Physiology Suppl, vol. 114, 1997, p. 267, XP002128629.

Saito K. et al., Comptes Rendus De L'Academie Des Sciences, vol. 319 (1996) pp. 969–973.

Saito et al., Plant Physiology, No. 106, Jan. 1, 1994, pp. 887–895, XP002078205.

Saito K., Stress Responses of Photosynthetic Organisms (1998) pp. 215–226, XP002121796.

Yamamoto K. and Sasaki T., EMBL Database, Jun. 7, 1999, XP002128630.

Yu Y. et al., EMBL Database, Jul. 2, 1999, XP002128631.

* cited by examiner

```
                         1                                                           60
SEQ ID NO:4    MASM--ATRFTKSSSPFHSITRTSNPHFAAPV------KISISRSSKART---------------
SEQ ID NO:6    MTSM--ATFFAQTSFPSHSLSKTFDTHFAPAP------KVNVFVNFRARR---------------
SEQ ID NO:8    MTSM--ATFFAQTSFPSHSLSKTFDTHFAPAP------KVNVFVNFRARR---------------
SEQ ID NO:11   MASL------FLKTPGPSQSLPKTHKTHFVLPQ------NLPLSWRSKYRAG-------------
SEQ ID NO:12   MSLMIRSSYVSHITLFQPRNSK----------PSSFTNQISFLSSSNNNPFLNLVYKRNLT 61                                                          120
SEQ ID NO:4    --PLR-LRVSAGLIEPDGGRLVELLVEEPL---RGLKKREALSLP-RIELSSIDIQWVHVL
SEQ ID NO:6    ---HVG-VRVSNALIEPDGGKLVELVVTDFE--RDLKKGEALSLP-RIKLSRIDLEWVHVL
SEQ ID NO:8    ---HVG-VRVSNALIEPDGGKLVELVVTDFE--RDLKKGEALSLP-RIKLSRIDLEWVHVL
SEQ ID NO:11   ---PAA-ARIRCGLIEPDGGKLVELIVEEPQ--RDLKRRQALSLP-QIKLSKIDIQWVHVL
SEQ ID NO:12   MQSVSKMTVKSSLIDPDGGELVELIVPETE--IGVKKAESETMP-KVKLNQIDLEWVHVI 121                                                         180
SEQ ID NO:4    SEGWASPLTGFMRESEFLQTLHFNSLRLPDGSVANMSVPIVLAIDDAQKHRI--ADSTSV
SEQ ID NO:6    SEGWATPLKGFMREAEFLQTLHFNSLRLDDGSVVNMSVPIVLAIDDAQKHRI--GDNKKV
SEQ ID NO:8    SEGWATPLKGFMREAEFLQTLHFNSLRLDDGSVVNMSVPIVLAIDDAQKHRI--GDNKKV
SEQ ID NO:11   SEGWASPLKGFMRESEFLQTLHFNSLRLGDGSVVNMSVPIVLAIDDSNKNNI--GDSSSV
SEQ ID NO:12   SEGWASPLKGFMREDEYLQSLHFNSLRLKNGTFVNMSLPIVLAIDDDTKEQI--GSSENV 181                                                         240
SEQ ID NO:4    ALFDANNNPIAILKDIEIYKHPEEERIARTWGTTAPGLPYVDQAITNAGNWLIGGDLEVI
SEQ ID NO:6    ALFDSKGDPVAILNNIEIYKHPKEERIARTWGTIAPGLTYVEQTITNAGNWLIGGDLEVI
SEQ ID NO:8    ALFDSKGDPVAILNNIEIYKHPKEERIARTWGTIAPGLTYVEQTITNAGNWLIGGDLEVI
SEQ ID NO:11   ALVDDKDNPIAILNDIEIYKHNKEERTARTWGTTAPGLPYAEQAITHAGNWLIGGDLEVI
SEQ ID NO:12   ALVCPQGDIIGSLRSVEIYKHNKEERIARTWGTTSPGLPYVEEYITPSGNWLIGGDLEVF
```

FIG. 1A

```
                    241                                                                              300
SEQ ID NO:4    EPIKYHDGLDRFRQSPAELREEFTRRNADAVFAFQLRNPVHNGHALLMTDTRRRLLDMGY
SEQ ID NO:6    EPIQYNDGLDHFRLSPAQLRAEFTRRNADAVFAFQLRNPVHNGHALLMTDTRKRLLEMGY
SEQ ID NO:8    EPIQYNDGLDHFRLSPAQLRAEFTRRNADAVFAFQLRNPVHNGHALLMTDTRKRLLEMGY
SEQ ID NO:12   EPIKYHDGLDRFRLSPAELRDEFTRRNADAVFAFQLRNPVHNGHALLMTDTRRRLLEMGY
SEQ ID NO:13   EPIKYNDGLDHYRLSPKQLREEFDNRQADAVFAFQLRNPVHNGHALLMNDTRKRLLEMGY 301                                                                              360
SEQ ID NO:4    KNPILLLHPLGGYTKADDVPLSWRMKQHEKVLEDGVLDPETTVVSIFPSPMHYAGPTEVQ
SEQ ID NO:6    KNPVLLLHPLGGYTKADDVPLDWRMKQHEKVLEDGVLDPETTVVSIFPSPMHYAGPTEVQ
SEQ ID NO:8    KNPVLLLHPLGGYTKADDVPLDWRMKQHEKVLEDGVLDPETTVVSIFPSPMHYAGPTEVQ
SEQ ID NO:11   KNPVLLLHPLGGYTKADDVPLEWRMKQHEMVLEDGVLDPETTVVSIFPSPMHYAGPTEVQ
SEQ ID NO:12   KNPVLLLHPLGGFTKADDVPLDVRMEQHSKVLEDGVLDPKTTIVSIFPSPMHYAGPTEVQ 361                                                                              420
SEQ ID NO:4    WHAKARINAGANFYIVGRDPAGMGHPTEKRDLYDADHGKKVLSMAPGLERLNILPFRVAA
SEQ ID NO:6    WHAKARINAGANFYIVGRDPAGMSHPVEKRDLYDADHGKKVLSMAPGLERLNILPFRVAA
SEQ ID NO:8    WHAKARINAGANFYIVGRDPAGMSHPVEKRDLYDADHGKKVLSMAPGLERLNILPFRVAA
SEQ ID NO:11   WHAKARINAGANFYIVGRDPAGMGHPLEKRDLYDADHGKKVLSMAPGLERLNILPFKVAA
SEQ ID NO:12   WHAKARINAGANFYIVGRDPAGMGHPTEKRDLYDPDHGKRVLSMAPGLEKLNILPFRVAA 421                                                                              480
SEQ ID NO:4    YDKTQGKMAFFDPSRPQDFLFISGTKMRTLAKNKENPPEGFMCPGGWKVLVEYYDSLVPA
SEQ ID NO:6    YDKTQGKMAFFDPSRPQDFLFISGTKMRTLARNKESPPDGFMCPGGWKVLVDYDSLVLS
SEQ ID NO:8    YDKTQGKMAFFDPSRPQDFLFISGTKMRTLARNKESPPDGFMCPGGWKVLVDYDSLVLS
SEQ ID NO:11   YDKTQNGMAFFDPSRPQDFLFISGTKMRALAKNKENPPDGFMCPGGWKVLVDYDSLTPS
SEQ ID NO:12   YDTIEKKMAFFDPSRAKEFLFISGTKMRTYARTGENPPDGFMCPSGWNVLVKYYESL--Q
```

FIG. 1B

```
              481           492
SEQ ID NO:4   S-NDRLPEPVLA
SEQ ID NO:6   S-NGKVQEAVPA
SEQ ID NO:8   S-NGKVQEAVPA
SEQ ID NO:11  E-NGRVPEPVPV
SEQ ID NO:12  ESEAKQQAVVSA
```

FIG. 1C

SEQUENCE LISTING

```
<160> NUMBER OF SEQ ID NOS: 12

<210> SEQ ID NO 1
<211> LENGTH: 516
<212> TYPE: DNA
<213> ORGANISM: Zea mays
<220> FEATURE:
<221> NAME/KEY: unsure
<222> LOCATION: (479)
<220> FEATURE:
<221> NAME/KEY: unsure
<222> LOCATION: (495)
<220> FEATURE:
<221> NAME/KEY: unsure
<222> LOCATION: (508)

<400> SEQUENCE: 1
tgatggtcta gatcagtatc gcctgtctcc agcacagctg cgtgaagagt ttgccaggcg      60
caatgctgat gcagtatttg cctttcagct tcgcaatcca gtacacaatg ggcatgctct     120
acttatgacc gacacacgca aacgcctcct tgagatgggt tataaaaacc ctgttcttct     180
gctccatcca ctgggaggat tcacaaaagc agatgatgtg cctcttagtt ggagaatgaa     240
gcaacatgag aaggttcttg aggaaggtgt cctcaaccca gaatcaactg ttgttgcgat     300
cttcccctct cctatgcatt atgctgggcc aactgaggtt caatggcatg ctaaggctcg     360
tattaatgct ggcgcaaatt tctatatcgt tggaagggat ctgctggtat gagcacccac     420
agagaaaagg actctatgat gctgatcacg gaaagaaggt ttgagcatgg ctcctggcnt     480
gagaggtcaa ctccntcctt caagtggntg ctataa                              516

<210> SEQ ID NO 2
<211> LENGTH: 133
<212> TYPE: PRT
<213> ORGANISM: Zea mays

<400> SEQUENCE: 2

Asp Gly Leu Asp Gln Tyr Arg Leu Ser Pro Ala Gln Leu Arg Glu Glu
  1               5                  10                  15

Phe Ala Arg Arg Asn Ala Asp Ala Val Phe Ala Phe Gln Leu Arg Asn
             20                  25                  30

Pro Val His Asn Gly His Ala Leu Leu Met Thr Asp Thr Arg Lys Arg
         35                  40                  45

Leu Leu Glu Met Gly Tyr Lys Asn Pro Val Leu Leu Leu His Pro Leu
     50                  55                  60
```

-continued

```
Gly Gly Phe Thr Lys Ala Asp Asp Val Pro Leu Ser Trp Arg Met Lys
 65                  70                  75                  80

Gln His Glu Lys Val Leu Glu Glu Gly Val Leu Asn Pro Glu Ser Thr
                 85                  90                  95

Val Val Ala Ile Phe Pro Ser Pro Met His Tyr Ala Gly Pro Thr Glu
            100                 105                 110

Val Gln Trp His Ala Lys Ala Arg Ile Asn Ala Gly Ala Asn Phe Tyr
        115                 120                 125

Ile Val Gly Arg Asp
    130

<210> SEQ ID NO 3
<211> LENGTH: 2280
<212> TYPE: DNA
<213> ORGANISM: Momordica charantia

<400> SEQUENCE: 3
gcacgaggtc ttcttcatca atttctgagt tcagtttctc cataacctcg ctttgaggcc     60
ttggtctcca tctcagatgg cgtccatggc gactcgtttc accaaatcct catccccatt    120
tcattctatt accagaacat ccaatcccca tttcgccgct ccggtgaaaa tctcaatttc    180
tcggagctcc aaggcgagga cccccctccg gctccgggtc tcggccgggt tgatcgaacc    240
ggacggcgga aggctggtgg agcttctggt tgaggagcct ctgaggggtt tgaagaagag    300
ggaggcctta tccttgccca gaatcgagct ctccagcatc gatatccagt gggttcatgt    360
gctcagcgaa ggctgggcca gccctctcac cggattcatg agagaatccg agttcctcca    420
aacgcttcat ttcaattccc tcaggctccc ggatgggtct gtggcgaata tgtcagtgcc    480
cattgttctc gccattgacg atgcccaaaa gcaccgcatc gccgactcca cttctgtcgc    540
tctctttgac gccaacaaca atcccatcgc cattctcaaa gatattgaga tctacaagca    600
ccctgaagaa gaaaggatag caagaacctg gggcaccact gccccaggac tcccttacgt    660
tgatcaagct ataaccaatg ctggtaattg gctgattggg ggtgatttgg aggttataga    720
accaatcaag taccatgatg gtctggaccg tttccgacag tcacctgcag aactacggga    780
ggaatttacc cggcgaaatg cagatgcagt atttgcattc caacttcgca atccagtcca    840
taacgggcat gctttactaa tgactgacac ccgccgtcgg ctgctcgata tggggtacaa    900
gaaccccatt ttgttgcttc atcctctggg tggctacacc aaggcagatg atgttccact    960
tagttggcga atgaagcaac atgagaaggt gcttgaggat ggtgttcttg atccagagac   1020
aacggtggtc tccatatttc catctccaat gcactatgca gggccaacag aggtgcagtg   1080
gcatgcaaag gcgagaatca atgcaggggc taacttttac attgttggcc gtgaccctgc   1140
tggaatgggt catcctactg agaaaaggga tctgtatgat gctgaccatg ggaagaaagt   1200
actgagcatg gcacctggac tggagcggct aaacatcctt cctttcagag ttgctgctta   1260
tgataaaact cagggcaaaa tggccttttt cgatccctcg agacctcagg atttcctttt   1320
catatccggc accaagatga gaacactagc aaagaacaaa gagaatccac cagaagggtt   1380
tatgtgccca gggggatgga aggtgttggt tgaatattat gacagtttgg tacctgcaag   1440
caatgacaga cttcctgaac ctgttctagc ttaggctgct gtatcagggg aaaagttatt   1500
agaaatttta aacatactgt gccagtgatg aataagatca tgaggcgatg gtacagaagc   1560
ataatataat ttgcctcact ttgtaaatta gatgccctca tcgcatcttt ggctttccta   1620
caagacaaca tattgtgtgt aatagtaagt gctttatgtt cagtgctatg aaggagatgg   1680
```

-continued

```
gtttgatgat ggatttggtt ttgaggttaa acaactttac tgaatgtact taatatatta    1740
tgaatttatt tttatattaa aaaaaaaaaa aaaaaactca gactagttct ctcctcgtgc    1800
cgaattcggc acgaggtaaa atgttggtga atgtgactgc tgatcaccga atagtttacg    1860
gtgctgagct ggctgccttc cttcagacct tcgcaaagat agttgagaat ccagaaagcc    1920
tgaccttgta gaagtcttca cgttgcaagt ttgaacattg gttaagactt gactgcaaga    1980
agaagggaaa aacagaatct ttctttcggc tgcggaatga tgaaagttta agttaaacag    2040
agtcccagag gaatcctttt tgtgcaggag gtcccaccga tacttttatt tgttacactt    2100
aatttagttc tattttttaaa agatttgaag agcaataatg agctgatttt tgtttccaag    2160
ttattgcgta cgggaaatgt attagtagaa actctgtgga tgaaagggaa tggtctcatt    2220
caattgacga aggtatttta tttaaaaaaa aaaaaaaaaa aaaaaaaaaa aaaaaaaaa     2280
```

<210> SEQ ID NO 4
<211> LENGTH: 465
<212> TYPE: PRT
<213> ORGANISM: Momordica charantia

<400> SEQUENCE: 4

```
Met Ala Ser Met Ala Thr Arg Phe Thr Lys Ser Ser Pro Phe His
 1               5                  10                  15

Ser Ile Thr Arg Thr Ser Asn Pro His Phe Ala Ala Pro Val Lys Ile
            20                  25                  30

Ser Ile Ser Arg Ser Ser Lys Ala Arg Thr Pro Leu Arg Leu Arg Val
        35                  40                  45

Ser Ala Gly Leu Ile Glu Pro Asp Gly Gly Arg Leu Val Glu Leu Leu
    50                  55                  60

Val Glu Glu Pro Leu Arg Gly Leu Lys Lys Arg Glu Ala Leu Ser Leu
65                  70                  75                  80

Pro Arg Ile Glu Leu Ser Ser Ile Asp Ile Gln Trp Val His Val Leu
                85                  90                  95

Ser Glu Gly Trp Ala Ser Pro Leu Thr Gly Phe Met Arg Glu Ser Glu
            100                 105                 110

Phe Leu Gln Thr Leu His Phe Asn Ser Leu Arg Leu Pro Asp Gly Ser
        115                 120                 125

Val Ala Asn Met Ser Val Pro Ile Val Leu Ala Ile Asp Asp Ala Gln
    130                 135                 140

Lys His Arg Ile Ala Asp Ser Thr Ser Val Ala Leu Phe Asp Ala Asn
145                 150                 155                 160

Asn Asn Pro Ile Ala Ile Leu Lys Asp Ile Glu Ile Tyr Lys His Pro
                165                 170                 175

Glu Glu Glu Arg Ile Ala Arg Thr Trp Gly Thr Thr Ala Pro Gly Leu
            180                 185                 190

Pro Tyr Val Asp Gln Ala Ile Thr Asn Ala Gly Asn Trp Leu Ile Gly
        195                 200                 205

Gly Asp Leu Glu Val Ile Glu Pro Ile Lys Tyr His Asp Gly Leu Asp
    210                 215                 220

Arg Phe Arg Gln Ser Pro Ala Glu Leu Arg Glu Phe Thr Arg Arg
225                 230                 235                 240

Asn Ala Asp Ala Val Phe Ala Phe Gln Leu Arg Asn Pro Val His Asn
                245                 250                 255

Gly His Ala Leu Leu Met Thr Asp Thr Arg Arg Arg Leu Leu Asp Met
            260                 265                 270
```

```
Gly Tyr Lys Asn Pro Ile Leu Leu His Pro Leu Gly Gly Tyr Thr
            275                 280                 285

Lys Ala Asp Asp Val Pro Leu Ser Trp Arg Met Lys Gln His Glu Lys
        290                 295                 300

Val Leu Glu Asp Gly Val Leu Asp Pro Glu Thr Thr Val Val Ser Ile
305                 310                 315                 320

Phe Pro Ser Pro Met His Tyr Ala Gly Pro Thr Glu Val Gln Trp His
                325                 330                 335

Ala Lys Ala Arg Ile Asn Ala Gly Ala Asn Phe Tyr Ile Val Gly Arg
            340                 345                 350

Asp Pro Ala Gly Met Gly His Pro Thr Glu Lys Arg Asp Leu Tyr Asp
        355                 360                 365

Ala Asp His Gly Lys Lys Val Leu Ser Met Ala Pro Gly Leu Glu Arg
    370                 375                 380

Leu Asn Ile Leu Pro Phe Arg Val Ala Ala Tyr Asp Lys Thr Gln Gly
385                 390                 395                 400

Lys Met Ala Phe Phe Asp Pro Ser Arg Pro Gln Asp Phe Leu Phe Ile
                405                 410                 415

Ser Gly Thr Lys Met Arg Thr Leu Ala Lys Asn Lys Glu Asn Pro Pro
            420                 425                 430

Glu Gly Phe Met Cys Pro Gly Gly Trp Lys Val Leu Val Glu Tyr Tyr
        435                 440                 445

Asp Ser Leu Val Pro Ala Ser Asn Asp Arg Leu Pro Glu Pro Val Leu
    450                 455                 460

Ala
465

<210> SEQ ID NO 5
<211> LENGTH: 1697
<212> TYPE: DNA
<213> ORGANISM: Glycine max

<400> SEQUENCE: 5
gcacgagaca aaatttgggt gcgtcctgga ttgacccttt tgcccccctct cccctcaccct     60 ccactaactc ctccttttg gttttttataa agcacattcc caatagagga gggtccctac    120
acaacacaac ccttcaatga cgtccatggc cactttcttc gcccaaacct ccttcccctc    180
ccactctctc tccaaaacct tcgatacccca tttcgcccct gccccgaaag tcaacgtctt    240
tgtgaacttc agggcgagga ggcacgttgg ggtgcgagtt tcgaacgcgc tgatcgaacc    300
agatggaggg aagctcgtgg agcttgtggt gacggatttt gagagggatt tgaagaaggg    360
tgaggctctt tcgttgccga ggatcaagct ctcaaggatt gaccttgagt gggtccatgt    420
cctcagcgaa ggatgggcca caccctgaa aggcttcatg agagaagccg agttcctcca    480
aacgcttcat ttcaactcgc tccgactcga tgatgggtcg tcgtgaaca tgtcagtgcc    540 catcgtgctg gctattgatg atgcgcagaa gcatcggatc ggggataaca aaaaggttgc    600 tcttttgat tccaagggag accccgttgc aattctcaat aatattgaga tttataagca    660
tcctaaagaa gaaagaatag cccgaacttg gggaaccatt gcccctggcc taccttatgt    720
tgaacaaact ataaccaatg ctggaaattg gttgattggg ggtgacctag aggtcattga    780
accaattcag tacaatgatg gacttgatca ttttcgtcta tctccggcac aactccgtgc    840
agagttcaca aggcgcaatg cggatgctgt gtttgccttc cagctccgga atcctgttca    900
caatggccat gctttgctaa tgactgacac ccgaaagcgc cttcttgaga tgggctataa    960
```

-continued

```
gaatcctgtc ctcttgcttc atccacttgg aggctacacc aaagctgatg atgtcccact    1020
tgattggcga atgaagcaac atgagaaggt acttgaggat ggtgttcttg atccagagac    1080
aactgtggta tccatattcc catctcccat gcactatgct ggacccacgg aggtgcagtg    1140
gcatgcaaag gctaggatca atgcaggggc taacttctat atcgttggtc gtgaccccgc    1200
aggcatgagc catccagttg agaaaagaga tctgtatgat gctgaccatg gaaagaaagt    1260
attgagcatg gcaccgggac tagagcgtct aaacattctt cctttcaggg ttgctgcata    1320
tgacaagact cagggtaaaa tggcattctt tgacccttca aggcctcagg acttcctgtt    1380
catatcaggc acaaagatgc gcacactggc aaggaacaaa gaaagtcctc ctgatggatt    1440
tatgtgccct ggtggatgga aggtgctggt tgattactat gatagcttag tactctcaag    1500
caacggcaaa gtgcaggaag ctgttccagc ttaatcttgt atcatatcat aatgtatata    1560
tctcatgatt gggagaaacc ttaagcttat gtattctcct gctaagacat acttcacgag    1620
gatcctctgg cccaatctaa taataataat aaattaaaac tttggggagg caaaaaaaaa    1680
aaaaaaaaaa aaaaaaa                                                   1697
```

<210> SEQ ID NO 6
<211> LENGTH: 465
<212> TYPE: PRT
<213> ORGANISM: Glycine max

<400> SEQUENCE: 6

```
Met Thr Ser Met Ala Thr Phe Phe Ala Gln Thr Ser Phe Pro Ser His
  1               5                  10                  15

Ser Leu Ser Lys Thr Phe Asp Thr His Phe Ala Pro Ala Pro Lys Val
                 20                  25                  30

Asn Val Phe Val Asn Phe Arg Ala Arg Arg His Val Gly Val Arg Val
             35                  40                  45

Ser Asn Ala Leu Ile Glu Pro Asp Gly Lys Leu Val Glu Leu Val
         50                  55                  60

Val Thr Asp Phe Glu Arg Asp Leu Lys Lys Gly Glu Ala Leu Ser Leu
 65                  70                  75                  80

Pro Arg Ile Lys Leu Ser Arg Ile Asp Leu Glu Trp Val His Val Leu
                 85                  90                  95

Ser Glu Gly Trp Ala Thr Pro Leu Lys Gly Phe Met Arg Glu Ala Glu
            100                 105                 110

Phe Leu Gln Thr Leu His Phe Asn Ser Leu Arg Leu Asp Asp Gly Ser
        115                 120                 125

Val Val Asn Met Ser Val Pro Ile Val Leu Ala Ile Asp Asp Ala Gln
    130                 135                 140

Lys His Arg Ile Gly Asp Asn Lys Lys Val Ala Leu Phe Asp Ser Lys
145                 150                 155                 160

Gly Asp Pro Val Ala Ile Leu Asn Asn Ile Glu Ile Tyr Lys His Pro
                165                 170                 175

Lys Glu Glu Arg Ile Ala Arg Thr Trp Gly Thr Ile Ala Pro Gly Leu
            180                 185                 190

Thr Tyr Val Glu Gln Thr Ile Thr Asn Ala Gly Asn Trp Leu Ile Gly
        195                 200                 205

Gly Asp Leu Glu Val Ile Glu Pro Ile Gln Tyr Asn Asp Gly Leu Asp
    210                 215                 220

His Phe Arg Leu Ser Pro Ala Gln Leu Arg Ala Glu Phe Thr Arg Arg
225                 230                 235                 240
```

Asn Ala Asp Ala Val Phe Ala Phe Gln Leu Arg Asn Pro Val His Asn
            245                 250                 255

Gly His Ala Leu Leu Met Thr Asp Thr Arg Lys Arg Leu Leu Glu Met
            260                 265                 270

Gly Tyr Lys Asn Pro Val Leu Leu Leu His Pro Leu Gly Gly Tyr Thr
            275                 280                 285

Lys Ala Asp Asp Val Pro Leu Asp Trp Arg Met Lys Gln His Glu Lys
290                 295                 300

Val Leu Glu Asp Gly Val Leu Asp Pro Glu Thr Thr Val Val Ser Ile
305                 310                 315                 320

Phe Pro Ser Pro Met His Tyr Ala Gly Pro Thr Glu Val Gln Trp His
            325                 330                 335

Ala Lys Ala Arg Ile Asn Ala Gly Ala Asn Phe Tyr Ile Val Gly Arg
            340                 345                 350

Asp Pro Ala Gly Met Ser His Pro Val Glu Lys Arg Asp Leu Tyr Asp
            355                 360                 365

Ala Asp His Gly Lys Lys Val Leu Ser Met Ala Pro Gly Leu Glu Arg
            370                 375                 380

Leu Asn Ile Leu Pro Phe Arg Val Ala Ala Tyr Asp Lys Thr Gln Gly
385                 390                 395                 400

Lys Met Ala Phe Phe Asp Pro Ser Arg Pro Gln Asp Phe Leu Phe Ile
            405                 410                 415

Ser Gly Thr Lys Met Arg Thr Leu Ala Arg Asn Lys Glu Ser Pro Pro
            420                 425                 430

Asp Gly Phe Met Cys Pro Gly Gly Trp Lys Val Leu Val Asp Tyr Tyr
            435                 440                 445

Asp Ser Leu Val Leu Ser Ser Asn Gly Lys Val Gln Glu Ala Val Pro
    450                 455                 460

Ala
465

<210> SEQ ID NO 7
<211> LENGTH: 1890
<212> TYPE: DNA
<213> ORGANISM: Triticum aestivum

<400> SEQUENCE: 7

```
gcacgaggcc gcacccgcac cggagcgtcg gtccgtcgaa cacctagcag gcagccatgg    60
ccctccacct cctcactccc acccaccctcc accacccctc gtgccgggcc acgccgcgcc   120
ggcatgtcgg ccatccgcag ctcgctcatc gacccggacg gcggcgcgct cgtcgacctc   180
gtggcgccgc cggggagccg cgcggcgctg cgggccgagg cggaggcgct cccgcgggtg   240
cggctcgcgg ccgtggacgt ggagtgggcg cacgtgctcg ccgagggctg ggcgtccccg   300
ctgcgcggct tcatgcggga gcacgagtac ctccagtgcc tccacttcaa ctccctccgc   360
ctcccctccg cggcctcgc caacatgtcg ctccccatcg tgctcgccgt cgacgacgcc   420
gccaaggacc gcgtcggcgc cgcccccgac gtcgcgctcg ccgggcccga cggcgagctc   480
ctcgccgtcc tccgcagtgt cgaaatatac cctcacaata agaagaaag gattgcaaga   540
acatggggga caactgcgcc tggcttacct tatgtcgatg aggcgataac accagctgga   600
aactggctga ttggtggtga tctggaggtg ttgcaaccca ttaagtataa cgatggcctt   660
gaccattaca ggctttcacc ccagcaactt agggacgaat cgacaagcg tggggctgat   720
gctgtatttg cattccagtt gagaaaccca gtccacaatg gcatgcact gttgatgaat   780
```

-continued

```
gacactagaa ggcgtctctt ggaaatgggt ttcaagaatc ccattctact gctacacccc    840
ttgggtggtt ttacaaaagc tgatgatgtc ccgctgcctg ttagaatgga acaacacagc    900
aaggtcttag aagatggagt ccttgacccc gagaccacta tcgtgtctat atttccctcc    960
ccaatgcatt atgctggtcc agcagaagtg cagtggcatg caaaggcacg aattaacgcc   1020
ggtgctaatt tctacatagt gggtcgtgat ccagctggga tgggccatcc gacagagaag   1080
agagatctgt acaacccaga ccatgggaag aaggtcctaa gcatggcccc cggtttggag   1140
aaactcaaca tattgccctt caaggtagca gcatatgata cggtggccaa gaagatggct   1200
ttctttgaac cttcacgcag tcaagatttt ctgttcatct caggaaccaa gatgcgcact   1260
ttcgccaaaa ctggagagaa ccctcctgat ggtttcatgt gccctggtgg gtggaaggtt   1320
cttgttgact actacaatag cttgcaaact gaaggagcta ccgcccccgc cgctgctact   1380
gtatgagaca agctgctgca tggctttgag atcatttgtt cgccggccag aaatggtgaa   1440
tgcaggggat tttaaaaccg ttccttcttt ttttccgccc tttcttttaa gttttttttgt   1500 aggttgctag tttattgatg ccatcagatc ctccaattgt tcaaattttt tctttcaaaa   1560
tagaaagaaa gattttgaag cttggcactg gaactcaaaa ctgttaacag atcgagcggt   1620
cgcaaattct gttattatcc tgtgatgact ctgacagtcc aactagccaa taaagaagtt   1680
cattgcaact gtgggagctc atccaagatc agactgcaat taatatccat attatgacac   1740
aacggagtgg cagagttggc attacggtgg attattagat gatgacagtc caacttatca   1800
atttagtttt tgtactatat tcgacaaagc ctcccgattc aggatttaaa caagaaata    1860 cttataatta tcaaaaaaaa aaaaaaaaaa                                    1890
```

<210> SEQ ID NO 8
<211> LENGTH: 461
<212> TYPE: PRT
<213> ORGANISM: Triticum aestivum

<400> SEQUENCE: 8

Ala Arg Gly Arg Thr Arg Thr Gly Ala Ser Val Arg Arg Thr Pro Ser
 1               5                  10                  15

Arg Gln Pro Trp Pro Ser Thr Ser Ser Leu Pro Pro Thr Ser Thr Thr
                20                  25                  30

Pro Arg Ala Gly Pro Arg Arg Ala Gly Met Ser Ala Ile Arg Ser Ser
            35                  40                  45

Leu Ile Asp Pro Asp Gly Ala Leu Val Asp Leu Val Ala Pro Pro
        50                  55                  60

Gly Ser Arg Ala Ala Leu Arg Ala Glu Ala Glu Ala Leu Pro Arg Val
65                  70                  75                  80

Arg Leu Ala Ala Val Asp Val Glu Trp Ala His Val Leu Ala Glu Gly
                85                  90                  95

Trp Ala Ser Pro Leu Arg Gly Phe Met Arg Glu His Glu Tyr Leu Gln
            100                 105                 110

Cys Leu His Phe Asn Ser Leu Arg Leu Pro Ser Gly Gly Leu Ala Asn
        115                 120                 125

Met Ser Leu Pro Ile Val Leu Ala Val Asp Ala Ala Lys Asp Arg
    130                 135                 140

Val Gly Ala Ala Pro Asp Val Ala Leu Ala Gly Pro Asp Gly Glu Leu
145                 150                 155                 160

Leu Ala Val Leu Arg Ser Val Glu Ile Tyr Pro His Asn Lys Glu Glu
                165                 170                 175

-continued

```
Arg Ile Ala Arg Thr Trp Gly Thr Thr Ala Pro Gly Leu Pro Tyr Val
            180                 185                 190

Asp Glu Ala Ile Thr Pro Ala Gly Asn Trp Leu Ile Gly Gly Asp Leu
            195                 200                 205

Glu Val Leu Gln Pro Ile Lys Tyr Asn Asp Gly Leu Asp His Tyr Arg
            210                 215                 220

Leu Ser Pro Gln Gln Leu Arg Asp Glu Phe Asp Lys Arg Gly Ala Asp
225                 230                 235                 240

Ala Val Phe Ala Phe Gln Leu Arg Asn Pro Val His Asn Gly His Ala
            245                 250                 255

Leu Leu Met Asn Asp Thr Arg Arg Leu Leu Glu Met Gly Phe Lys
            260                 265                 270

Asn Pro Ile Leu Leu His Pro Leu Gly Gly Phe Thr Lys Ala Asp
            275                 280                 285

Asp Val Pro Leu Pro Val Arg Met Glu Gln His Ser Lys Val Leu Glu
            290                 295                 300

Asp Gly Val Leu Asp Pro Glu Thr Thr Ile Val Ser Ile Phe Pro Ser
305                 310                 315                 320

Pro Met His Tyr Ala Gly Pro Ala Glu Val Gln Trp His Ala Lys Ala
            325                 330                 335

Arg Ile Asn Ala Gly Ala Asn Phe Tyr Ile Val Gly Arg Asp Pro Ala
            340                 345                 350

Gly Met Gly His Pro Thr Glu Lys Arg Asp Leu Tyr Asn Pro Asp His
            355                 360                 365

Gly Lys Lys Val Leu Ser Met Ala Pro Gly Leu Glu Lys Leu Asn Ile
            370                 375                 380

Leu Pro Phe Lys Val Ala Ala Tyr Asp Thr Val Ala Lys Lys Met Ala
385                 390                 395                 400

Phe Phe Glu Pro Ser Arg Ser Gln Asp Phe Leu Phe Ile Ser Gly Thr
            405                 410                 415

Lys Met Arg Thr Phe Ala Lys Thr Gly Glu Asn Pro Pro Asp Gly Phe
            420                 425                 430

Met Cys Pro Gly Gly Trp Lys Val Leu Val Asp Tyr Tyr Asn Ser Leu
            435                 440                 445

Gln Thr Glu Gly Ala Thr Ala Pro Ala Ala Thr Val
450                 455                 460

<210> SEQ ID NO 9
<211> LENGTH: 563
<212> TYPE: DNA
<213> ORGANISM: Triticum aestivum
<220> FEATURE:
<221> NAME/KEY: unsure
<222> LOCATION: (337)
<220> FEATURE:
<221> NAME/KEY: unsure
<222> LOCATION: (404)
<220> FEATURE:
<221> NAME/KEY: unsure
<222> LOCATION: (437)
<220> FEATURE:
<221> NAME/KEY: unsure
<222> LOCATION: (475)
<220> FEATURE:
<221> NAME/KEY: unsure
<222> LOCATION: (483)
<220> FEATURE:
<221> NAME/KEY: unsure
<222> LOCATION: (514)
<220> FEATURE:
<221> NAME/KEY: unsure
```

```
<222> LOCATION: (517)
<220> FEATURE:
<221> NAME/KEY: unsure
<222> LOCATION: (532)
<220> FEATURE:
<221> NAME/KEY: unsure
<222> LOCATION: (549)
<220> FEATURE:
<221> NAME/KEY: unsure
<222> LOCATION: (562)

<400> SEQUENCE: 9
ggaggccatt acaaatgctg gtgattggct gattggtgga gacctggagg ttatagaacc      60
aatcaagtat aatgatggtc tggatcagta tcgtttgtct ccatcacagc tgcgtgaaga    120
atttgccagg cgcaatgcag atgcagtatt tgcttttcaa cttcgtaacc ctgtgcacaa    180
tgggcatgcg ctgctcatga ctgatacacg gaggcgcctt cttgagatgg ctacaaaaa    240 ccctgttctt cttctccatc cactgggagg attcacaaag gcagatgacg tgcctcttag    300
tgtgagaatg aagcagcatg agaagttctt gaggaangtg tcctaaacca gatcaactgt    360
ggttgcatct cccttcacaa tgcatatctg ggcaactgag tcantggatg caagctgtat    420
atgctggtgc aaactcntat tgtcgaagga tctgctggta tgggcaccga cgaanagagg    480
acnttatgat ctatacggaa aaatctgata tggnccnggc tgaaagccat anctccttca    540
ggtgcgctnt aaaacataca gnt                                            563

<210> SEQ ID NO 10
<211> LENGTH: 110
<212> TYPE: PRT
<213> ORGANISM: Triticum aestivum

<400> SEQUENCE: 10

Glu Ala Ile Thr Asn Ala Gly Asp Trp Leu Ile Gly Gly Asp Leu Glu
  1               5                  10                  15

Val Ile Glu Pro Ile Lys Tyr Asn Asp Gly Leu Asp Gln Tyr Arg Leu
             20                  25                  30

Ser Pro Ser Gln Leu Arg Glu Glu Phe Ala Arg Arg Asn Ala Asp Ala
         35                  40                  45

Val Phe Ala Phe Gln Leu Arg Asn Pro Val His Asn Gly His Ala Leu
     50                  55                  60

Leu Met Thr Asp Thr Arg Arg Leu Leu Glu Met Gly Tyr Lys Asn
 65                  70                  75                  80

Pro Val Leu Leu Leu His Pro Leu Gly Gly Phe Thr Lys Ala Asp Asp
                 85                  90                  95

Val Pro Leu Ser Val Arg Met Lys Gln His Glu Lys Phe Leu
            100                 105                 110

<210> SEQ ID NO 11
<211> LENGTH: 463
<212> TYPE: PRT
<213> ORGANISM: Solanum tuberosum

<400> SEQUENCE: 11

Met Ala Ser Leu Phe Leu Lys Thr Pro Gly Pro Ser Gln Ser Leu Pro
  1               5                  10                  15

Lys Thr His Lys Thr His Phe Val Leu Pro Gln Asn Leu Pro Leu Ser
             20                  25                  30

Trp Arg Ser Lys Tyr Arg Ala Gly Pro Ala Ala Ala Arg Ile Arg Cys
         35                  40                  45
```

-continued

```
Gly Leu Ile Glu Pro Asp Gly Gly Lys Leu Val Glu Leu Ile Val Glu
 50                  55                  60

Glu Pro Gln Arg Asp Leu Lys Arg Arg Gln Ala Leu Ser Leu Pro Gln
 65                  70                  75                  80

Ile Lys Leu Ser Lys Ile Asp Ile Gln Trp Val His Val Leu Ser Glu
                 85                  90                  95

Gly Trp Ala Ser Pro Leu Lys Gly Phe Met Arg Glu Ser Glu Phe Leu
            100                 105                 110

Gln Thr Leu His Phe Asn Ser Leu Arg Leu Gly Asp Gly Ser Val Val
            115                 120                 125

Asn Met Ser Val Pro Ile Val Leu Ala Ile Asp Asp Ser Asn Lys Asn
        130                 135                 140

Asn Ile Gly Asp Ser Ser Val Ala Leu Val Asp Asp Lys Asp Asn
145                 150                 155                 160

Pro Ile Ala Ile Leu Asn Asp Ile Glu Ile Tyr Lys His Asn Lys Glu
                165                 170                 175

Glu Arg Thr Ala Arg Thr Trp Gly Thr Thr Ala Pro Gly Leu Pro Tyr
            180                 185                 190

Ala Glu Gln Ala Ile Thr His Ala Gly Asn Trp Leu Ile Gly Gly Asp
        195                 200                 205

Leu Glu Val Ile Glu Pro Ile Lys Tyr His Asp Gly Leu Asp Arg Phe
210                 215                 220

Arg Leu Ser Pro Ala Glu Leu Arg Asp Glu Phe Thr Arg Arg Asn Ala
225                 230                 235                 240

Asp Ala Val Phe Ala Phe Gln Leu Arg Asn Pro Val His Asn Gly His
                245                 250                 255

Ala Leu Leu Met Thr Asp Thr Arg Arg Arg Leu Leu Glu Met Gly Tyr
            260                 265                 270

Lys Asn Pro Val Leu Leu His Pro Leu Gly Gly Tyr Thr Lys Ala
        275                 280                 285

Asp Asp Val Pro Leu Glu Trp Arg Met Lys Gln His Glu Met Val Leu
290                 295                 300

Glu Asp Gly Val Leu Asp Pro Glu Thr Thr Val Val Ser Ile Phe Pro
305                 310                 315                 320

Ser Pro Met His Tyr Ala Gly Pro Thr Glu Val Gln Trp His Ala Lys
                325                 330                 335

Ala Arg Ile Asn Ala Gly Ala Asn Phe Tyr Ile Val Gly Arg Asp Pro
            340                 345                 350

Ala Gly Met Gly His Pro Leu Glu Lys Arg Asp Leu Tyr Asp Ala Asp
        355                 360                 365

His Gly Lys Lys Val Leu Ser Met Ala Pro Gly Leu Glu Arg Leu Asn
370                 375                 380

Ile Leu Pro Phe Lys Val Ala Ala Tyr Asp Lys Thr Gln Asn Gly Met
385                 390                 395                 400

Ala Phe Phe Asp Pro Ser Arg Pro Gln Asp Phe Leu Phe Ile Ser Gly
                405                 410                 415

Thr Lys Met Arg Ala Leu Ala Lys Asn Lys Glu Asn Pro Pro Asp Gly
            420                 425                 430

Phe Met Cys Pro Gly Gly Trp Lys Val Leu Val Asp Tyr Tyr Asp Ser
        435                 440                 445

Leu Thr Pro Ser Glu Asn Gly Arg Val Pro Glu Pro Val Pro Val
    450                 455                 460
```

-continued

```
<210> SEQ ID NO 12
<211> LENGTH: 476
<212> TYPE: PRT
<213> ORGANISM: Arabidopsis thaliana

<400> SEQUENCE: 12

Met Ser Leu Met Ile Arg Ser Ser Tyr Val Ser His Ile Thr Leu Phe
  1               5                  10                  15

Gln Pro Arg Asn Ser Lys Pro Ser Ser Phe Thr Asn Gln Ile Ser Phe
                 20                  25                  30

Leu Ser Ser Asn Asn Asn Pro Phe Leu Asn Leu Val Tyr Lys Arg
         35                  40                  45

Asn Leu Thr Met Gln Ser Val Ser Lys Met Thr Val Lys Ser Ser Leu
 50                  55                  60

Ile Asp Pro Asp Gly Gly Glu Leu Val Glu Leu Ile Val Pro Glu Thr
 65                  70                  75                  80

Glu Ile Gly Val Lys Lys Ala Glu Ser Glu Thr Met Pro Lys Val Lys
                 85                  90                  95

Leu Asn Gln Ile Asp Leu Glu Trp Val His Val Ile Ser Glu Gly Trp
            100                 105                 110

Ala Ser Pro Leu Lys Gly Phe Met Arg Glu Asp Glu Tyr Leu Gln Ser
        115                 120                 125

Leu His Phe Asn Ser Leu Arg Leu Lys Asn Gly Thr Phe Val Asn Met
    130                 135                 140

Ser Leu Pro Ile Val Leu Ala Ile Asp Asp Thr Lys Glu Gln Ile
145                 150                 155                 160

Gly Ser Ser Glu Asn Val Ala Leu Val Cys Pro Gln Gly Asp Ile Ile
                165                 170                 175

Gly Ser Leu Arg Ser Val Glu Ile Tyr Lys His Asn Lys Glu Glu Arg
            180                 185                 190

Ile Ala Arg Thr Trp Gly Thr Thr Ser Pro Gly Leu Pro Tyr Val Glu
        195                 200                 205

Glu Tyr Ile Thr Pro Ser Gly Asn Trp Leu Ile Gly Gly Asp Leu Glu
    210                 215                 220

Val Phe Glu Pro Ile Lys Tyr Asn Asp Gly Leu Asp His Tyr Arg Leu
225                 230                 235                 240

Ser Pro Lys Gln Leu Arg Glu Glu Phe Asp Asn Arg Gln Ala Asp Ala
                245                 250                 255

Val Phe Ala Phe Gln Leu Arg Asn Pro Val His Asn Gly His Ala Leu
            260                 265                 270

Leu Met Asn Asp Thr Arg Lys Arg Leu Leu Glu Met Gly Tyr Lys Asn
        275                 280                 285

Pro Val Leu Leu Leu His Pro Leu Gly Gly Phe Thr Lys Ala Asp Asp
    290                 295                 300

Val Pro Leu Asp Val Arg Met Glu Gln His Ser Lys Val Leu Glu Asp
305                 310                 315                 320

Gly Val Leu Asp Pro Lys Thr Thr Ile Val Ser Ile Phe Pro Ser Pro
                325                 330                 335

Met His Tyr Ala Gly Pro Thr Glu Val Gln Trp His Ala Lys Ala Arg
            340                 345                 350

Ile Asn Ala Gly Ala Asn Phe Tyr Ile Val Gly Arg Asp Pro Ala Gly
        355                 360                 365

Met Gly His Pro Thr Glu Lys Arg Asp Leu Tyr Asp Pro Asp His Gly
    370                 375                 380
```

-continued

```
Lys Arg Val Leu Ser Met Ala Pro Gly Leu Glu Lys Leu Asn Ile Leu
385                 390                 395                 400

Pro Phe Arg Val Ala Ala Tyr Asp Thr Ile Glu Lys Lys Met Ala Phe
            405                 410                 415

Phe Asp Pro Ser Arg Ala Lys Glu Phe Leu Phe Ile Ser Gly Thr Lys
            420                 425                 430

Met Arg Thr Tyr Ala Arg Thr Gly Glu Asn Pro Pro Asp Gly Phe Met
            435                 440                 445

Cys Pro Ser Gly Trp Asn Val Leu Val Lys Tyr Tyr Glu Ser Leu Gln
        450                 455                 460

Glu Ser Glu Ala Lys Gln Gln Ala Val Val Ser Ala
465                 470                 475
```

GENES ENCODING SULFATE ASSIMILATION PROTEINS

This application claims the benefit of U.S. Provisional Application Ser. No. 60/092,833, filed Jul. 14, 1998.

FIELD OF THE INVENTION

This invention is in the field of plant molecular biology. More specifically, this invention pertains to nucleic acid fragments encoding sulfate assimilation proteins in plants and seeds.

BACKGROUND OF THE INVENTION

Sulfate assimilation is the process by which environmental sulfur is fixed into organic sulfur for use in cellular metabolism. The two major end products of this process are the essential amino acids cysteine and methionine. These amino acids are limiting in food and feed; they cannot be synthesized by animals and thus must be acquired from plant sources. Increasing the level of these amino acids in feed products is thus of major economic value. Key to that process is increasing the level of organic sulfur available for cysteine and methionine biosynthesis.

Multiple enzymes are involved in sulfur assimilation. These include: High affinity sulfate transporter and low affinity sulfate transporter proteins which serve to transport sulfur from the outside environment across the cell membrane into the cell (Smith et al. (1995) *PNAS* 92(20):9373–9377). Once sulfur is in the cell sulfate adenylyltransferase (ATP sulfurylase; Bolchia et al. (1999) *Plant Mol. Biol.* 39(3):527–537) catalyzes the first step in assimilation, converting the inorganic sulfur into an organic form, adenosine-5' phosphosulfate (APS). Next, several enzymes further modify organic sulfur for use in the biosynthesis of cysteine and methionine. For example, adenylylsulfate kinase (APS kinase), catalyzes the conversion of APS to the biosynthetic intermediate PAPS (3'-phospho-adenosine-5' phosphosulfate; Arz et al. (1994) *Biochim. Biophy. Acta* 1218(3):447–452). APS reductase (5' adenylyl phosphosulphate reductase) is utilized in an alternative pathway, resulting in an inorganic but cellularly bound (bound to a carrier), form of sulfur (sulfite; Setya et al. (1996) *PNAS* 93(23):13383–13388). Sulfite reductase firther reduces the sulfite, still attached to the carrier, to sulfide and serine O-acetyltransferase converts serine to O-acetylserine, which will serve as the backbone to which the sulfide will be transferred to from the carrier to form cysteine (Yonelcura-Sakalibara et al. (1998) *J. Biolchem.* 124(3):615–621 and Saito et al. (1995) *J. Biol. Chem.* 270(27):16321–16326).

As described, each of these enzymes is involved in sulfate assimilation and the pathway leading to cysteine biosynthesis, which in turn serves as an organic sulfur donor for multiple other pathways in the cell, including methionine biosynthesis. Together or singly these enzymes and the genes that encode them have utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

The sequence of a corn ATP sulfurylase became available to the public after the instant invention was made (see Bolchi, A. et al. (1999) *Plant Mol. Biol.* 39 (3):527–537; NCBI Identifier No. gi 2738750).

SUMMARY OF THE INVENTION

The instant invention relates to isolated nucleic acid fragments encoding sulfate assimilation proteins. Specifically, this invention concerns an isolated nucleic acid fragment encoding an ATP sulfurylase (sulfate adenyltransferase) and an isolated nucleic acid fragment that is substantially similar to an isolated nucleic acid fragment encoding an ATP sulfurylase. In addition, this invention relates to a nucleic acid fragment that is complementary to the nucleic acid fragment encoding ATP sulfurylase. An additional embodiment of the instant invention pertains to a polypeptide encoding all or a substantial portion of an ATP sulfurylase.

In another embodiment, the instant invention relates to a chimeric gene encoding an ATP sulfurylase, or to a chimeric gene that comprises a nucleic acid fragment that is complementary to a nucleic acid fragment encoding an ATP sulfurylase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an ATP sulfurylase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an ATP sulfurylase in a transformed host cell comprising: a) transforming a host cell with a chimeric gene comprising a nucleic acid fragment encoding an ATP sulfurylase; and b) growing the transformed host cell under conditions that are suitable for expression of the chimeric gene wherein expression of the chimeric gene results in production of altered levels of ATP sulfurylase in the transformed host cell.

An addition embodiment of the instant invention concerns a method for obtaining a nucleic acid fragment encoding all or a substantial portion of an amino acid sequence encoding an ATP sulfurylase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1A–1C shows a comparison of the amino acid sequences set forth in SEQ ID NOS:2, 4, 6, 8 and 10 and the *Zea mays, Solanum tuberosum* and *Arabidopsis thaliana* sequences (SEQ ID NOS: 11, 12 and 13 respectively).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–825.

TABLE 1

Sulfate Assimilation Proteins

| Protein | Clone Designation | SEQ ID NO: (Nucleotide) | SEQ ID NO: (Amino Acid) |
| --- | --- | --- | --- |
| ATP sulfurylase | cta1n.pk0027.e11 | 1 | 2 |
| ATP sulfurylase | fds.pk0025.e8 | 3 | 4 |
| ATP sulfurylase | sr1.pk0096.f10 | 5 | 6 |
| ATP sulfurylase | Contig composed of: wlm96.pk0024.h9 wlmk8.pk0018.e8 | 7 | 8 |
| ATP sulfurylase | wre1n.pk0030.e7 | 9 | 10 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1X SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 90% identical to the amino acid sequences reported herein. Most preferred are those nucleic acid fragments whose nucleotide sequences encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization)

and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the MRNA precursor. The use of different 3' non-coding sequences is exemplified by Ingelbrecht et al. (1989) Plant Cell 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be traslated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et *al. Molecular Cloning. A Laboratory Manual;* Cold Spring Harbor Laboratory Press: Cold Spring Harbor, 1989 (hereinafter "Maniatis").

Nucleic acid fragments encoding at least a portion of several sulfate assimilation proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other ATP sulfurylase enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5'

RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of ATP sulfurylase in those cells. This enzyme is involved in sulfate assimilation and the pathway leading to cysteine biosynthesis, which in turn serves as an organic sulfir donor for multiple other pathways in the cell, including methionine biosynthesis. This enzyme and the gene(s) that encodes the protein has utility in overcoming the sulfur limitations known to exist in crop plants. It may be possible to modulate the level of sulfir containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sulfate assimilation protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J Hum. Genet.* 32:314–331).

The production and use of plant gene-derived probes for use in genetic mapping is described in Bernatzky and Tanksley (1986) *Plant Mol Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, Momordica, rice, soybean and wheat tissues were prepared. The characteristics of the libraries are described below.

TABLE 2 cDNA Libraries from Corn, Momordica, Rice, Soybean and Wheat

| Library | Tissue | Clone |
|---|---|---|
| cta1n | Corn (*Zea mays* L.) tassel* | cta1n.pk0027.e11 |
| fds | *Momordica charantia* developing seed | fds.pk0025.e8 |
| sr1 | Soybean (*Glycine max* L.) root library | sr1.pk0096.f10 |
| wlm96 | Wheat (*Triticum aestivum* L.) seedlings 96 hr after inoculation w/*E. graminis* | wlm96.pk0024.h9 |
| wlmk8 | Wheat (*Triticum aestivum* L.) seedlings 8 hr after inoculation w/*E. graminis* and teatment with fungicide** | wlmk8.pk0018.e8 |
| wreln | Wheat (*Triticum aestivum* L.) root; 7 day old etiolated seedling* | wreln.pk0030.e7 |

*These libraries were normalized essentially as described in U.S. Pat. No. 5,482,845, incorporated herein by reference.
**Fungicide: Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding sulfate assimilation proteins were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding ATP sulfurylase

The BLASTX search using the EST sequences from clones listed in Table 3 revealed similarity of the polypeptides encoded by the cDNAs to ATP sulfirylase from *Zea mays* (NCBI Identifier No. gi 2738750), *Solanum tuberosum* (NCBI Identifier No. gi 479090 and gi 629733) and *Arabidopsis thaliana* (NCBI Identifier No. gi 629562. Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Zea mays*, *Solanum tuberosum* and *Arabidopsis thaliana* ATP Sulfurylase

| Clone | Status | BLAST pLog Score |
|---|---|---|
| cta1n.pk0027.e11 | EST | 92.68 (gi 479090) |
| fds.pk0025.e8 | FIS | >254.00 (gi 629733) |
| sr1.pk0096.f10 | FIS | >254.00 (gi 629733) |
| Contig composed of: wlm96.pk0024.h9 wlmk8.pk0018.e8 | Contig | >254.00 (gi 629562) |
| wreln.pk0030.e7 | EST | 66.26 (gi 2738750) |

FIG. 1 presents an alignment of the amino acid sequences set forth in SEQ ID NOS: 4, 6 and 8 and the *Solanum tuberosum* and *Arabidopsis thaliana* sequences (SEQ ID NOS: 11 (gi 629733) and 12 (gi 629562) respectively). The data in Table 4 represents a calculation of the percent identity of the amino acid sequences set forth in SEQ ID NOS:4, 6 and 8 and the *Solanum tuberosum* and *Arabidopsis thaliana* sequences (SEQ ID NOS:11 and 12).

TABLE 4

Percent Identity of Amino Acid Sequences
Deduced From the Nucleotide Sequences
of cDNA Clones Encoding Polypeptides Homologous
to ATP Sulfurylase

| SEQ ID NO. | Percent Identity to |
| --- | --- |
| 4 | 82% (gi 629733) |
| 6 | 80% (gi 629733) |
| 8 | 71% (gi 629562) |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an ATP sulfurylase. These sequences represent the first corn, Momordica, rice, soybean and wheat sequences encoding ATP sulfurylase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR The amplified DNA is then digested with restriction enzymes NeoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL1-Blue (Epicurian Coi XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium.

These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *BioTechnology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 $\mu$g/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 $\mu$L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nuecotide sequence encoding a polypeptide having ATP sulfurylase activity, wherein the amino acid sequence of the polypeptide and the amino acid sequence of SEQ ID NO:4, SEQ ID NO.6, SEQ ID NO8, or SEQ ID NO:10 have at least 90% identity based on the Clustal alignment method with the default parameters, or
   (b) the complement of the nucleotide sequence.

2. The polynucleotide of claim 1, wherein the amino acid sequence of the polypeptide and the amino acid sequence of SEQ ID NO:4, SEQ ID NO:6, SEQ ID NO:8, or SEQ ID NO:10 have at least 95% identity based on the Clustal alignment method with the default parameters.

3. The polynucleotide of claim 1 comprising the nucleotide sequence of SEQ ID NO:3, SEQ ID NO:5, SEQ ID NO:7, or SEQ ID NO:9.

4. The polynucleotide of claim 1, wherein the polypeptide comprises the amino acid sequence of SEQ ID NO:4, SEQ ID NO:6, SEQ ID NO:8, or SEQ ID NO:10.

5. An isolated polynulcotide comprising:
   (a) a nucleotide sequence encoding a polypcptide having ATP sulfurylase activity, wherein the amino acid sequence of the polypeptide and the amino acid sequence of SEQ ID NO:2 have at least 95% identity based on the Clustal alignment method with the default parameters, or
   (b) the complement of the nucleotide sequence.

6. The polynucleotide of claim 5 comprising the nucleotide sequence of SEQ ID NO:1.

7. The polynucleotide of claim 5, wherein the polypeptide comprises the amino acid sequence of SEQ ID NO:2.

8. The polynucleotide of claim 1 or 5, wherein the polynucleotide is a functional RNA.

9. A chimeric gene comprising the polynucleotide of claim 1 or 5 operably linked to a regulatory sequence.

10. A vector comprising the polynucleotide of claim 1 or 5.

11. A method for transforming a cell comprising transforming a cell with the polynucleotide of claim 1 or 5.

12. The cell produced by the method of claim 11.

* * * * *

UNITED STATES PATENT AND TRADEMARK OFFICE
CERTIFICATE OF CORRECTION

PATENT NO.    : 6,338,966 B1
DATED         : January 15, 2002
INVENTOR(S)   : Saverio Carl Falco et al.

It is certified that error appears in the above-identified patent and that said Letters Patent is hereby corrected as shown below:

<u>Title page,</u>
Item [56], References Cited, OTHER PUBLICATIONS, insert the following:
-- Sandra Schiffmann et al., FEBS Lett., vol. 355:229-232, 1994, APS-sulfotransferase activity is identical to higher plant APS-kinase Jose F. Gutierrez-Marcos et al., PNAS, vol. 93:13377-13382, 11/1996, Three members of a novel small gene-family from Arabidopsis thaliana able to complement functionally an Escherichia coli mutant defective in PAPS reductase activity encode proteins with a thioredoxin-like domain and "APS reductase" activity Hideki Takahashi et al., Plant & Cell Phys., vol. 39(S148), 1998, Antisense Repression of Sulfate Transporter in Transgenic Arabidopsis thaliana Plants --

Signed and Sealed this

Twenty-fourth Day of December, 2002

JAMES E. ROGAN
*Director of the United States Patent and Trademark Office*